US00PP25601P3

(12) United States Plant Patent
Korlipara

(10) Patent No.: US PP25,601 P3
(45) Date of Patent: May 26, 2015

(54) *DICENTRA* PLANT NAMED 'AMORE PINK'

(50) Latin Name: ***Dicentra* hybrid**
Varietal Denomination: Amore Pink

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 177 days.

(21) Appl. No.: 13/986,956

(22) Filed: Jun. 18, 2013

(65) Prior Publication Data

US 2014/0373236 P1 Dec. 18, 2014

(51) Int. Cl.
*A01H 5/02* (2006.01)

(52) U.S. Cl.
USPC ..... Plt./426

(58) Field of Classification Search
USPC ..... Plt./426
See application file for complete search history.

*Primary Examiner* — Susan McCormick Ewoldt

(74) *Attorney, Agent, or Firm* — Klarquist Sparkman, LLP

(57) ABSTRACT

A new and distinct form of *Dicentra* plant characterized by its soft, feathery blue green foliage, a compact habit, medium large silver pink flowers on short flower stalks, repeat blooming, and good vigor.

1 Drawing Sheet

Botanical denomination: *Dicentra* hybrid.
Variety designation: 'Amore Pink'.

BACKGROUND OF THE INVENTION

The present invention relates to a new and distinct cultivar of *Dicentra*, of the family Fumariaceae, known by the cultivar name, 'Amore Pink'. This plant originated from planned cross. The seed parent is *Dicentra* 'Burning Hearts', U.S. Plant Pat. No. 20,797, and the pollen parent was a proprietary unreleased *Dicentra* hybrid seedling (*Dicentra peregrina* x (*D. formosa* subsp. *oregana* x *D. eximia*)). This seedling selection stood out with its unique characteristics.

This new cultivar is uniquely characterized by:

1. soft, feathery blue green foliage,
2. a compact habit,
3. medium large silver pink flowers on short flower stalks,
4. repeat blooming over a long season,
5. good vigor.

Compared to the seed parent, *Dicentra* 'Burning Hearts', U.S. Plant Pat. No. 20,797, the new cultivar a bigger habit, bigger and greener leaves, and silver pink rather than dark burgundy flowers.

Compared to the pollen parent the new cultivar has blue green foliage color rather than green and a tighter habit.

Compared to *Dicentra* 'Candy Hearts', U.S. Plant Pat. No. 14,692, the new cultivar has a bigger habit, bigger and greener leaves, and silver pink rather than pink flowers.

Compared to *Dicentra* 'Amore Rose', U.S. Ser. No. 13/986,999, the new cultivar has silver pink flowers rather than deep rose.

The new variety has been reproduced only by asexual propagation. Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eighteen-month-old *Dicentra* 'Amore Pink' in the trial bed in April in Canby, Oreg.

FIG. 2 shows a close up of the same plant.

DETAILED PLANT DESCRIPTION

The following is a detailed description of the new *Dicentra* cultivar based on observations of 9-month-old specimens grown in a cool greenhouse in gallon containers in May in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on *The Royal Horticultural Society Colour Chart*. The color descriptions are all based on *The Royal Horticultural Society Colour Chart*, 5$^{th}$ edition.

Plant:

*Type*.—Herbaceous perennial.
*Form*.—Clumping rosette.
*# crowns*.—3 to 4.
*Cold hardiness*.—U.S.D.A. Zone 5.
*Size*.—Foliage grows to 13 cm tall to top of foliage and 36 cm wide.
*Vigor*.—Excellent.

Leaf:

*Type*.—Ternately compound.
*Arrangement*.—Rosette.
*Shape*.—Broadly ovate to triangular in outline, leaflets usually ovate in outline.
*Lobing /division*.—17 to 30 leaflets per leaf, leaflets lobed and tip acute.
*Venation*.—Pinnate.

*Blade size*.—Grows to 13 cm long and 13 cm wide.

*Surface texture*.—Glabrous.

*Petiole description*.—Grows to 10 cm long and 2.5 mm wide, base clasping, Green N38B blending to base where tinted Greyed Orange 174A.

*Leaf color*.—Young leaves (including veins) top side closest to Green N138B, bottom side N138B; older leaves (including veins) topside closest to Green N138A, bottom side N138B.

Inflorescence:

*Type*.—Scapose panicle.

*Number of flowers*.—About 17 per panicle, increasing with older plants.

*Number of panicles in first spring flush*.—1 to 4.

*Peduncle description*.—Grows 19 cm to 25 cm long and 2.5 mm wide, glabrous, Yellow Green 144A tinted Greyed Orange 174A.

*Pedicel description*.—5 mm to 7 mm long, 2 mm wide, Yellow Green 144A.

*Bloom period*.—April to June in Canby, Oreg.

Flower Bud:

*Size*.—22 mm long and 11 mm wide at the widest point prior to opening.

*Description*.—Oblong with the base wider than the tip and heart-shaped.

*Color*.—Purple 76C.

Flower:

*Type*.—Zygomorphic.

*Corolla description*.—Pendulous, heart-shaped on bottom half, laterally compressed, 4 petals in 2 opposed pairs; outer petal pair pouched at the base forming the heart shape, reflexed on top ⅓ and cupped at tip, 16 mm long and spreading 20 mm wide on top, margins entire, tip acute, glabrous inside and out; outside color Purple 76C with Purple 75C on bottom edges, inside color Purple 76D on bottom ¾ and Violet 84B on top ¼ where cupped; inner petal pair tongue shaped and connected at the tip, 18 mm long and to 3 mm wide, with convex inner face and crested apex; margins entire, tip apiculate; inside Purple 76C on bottom ⅓, 76D on middle ⅓, and Violet 86A on top ⅓; outside Violet 84A lightening to Purple 76B on sides.

*Calyx description*.—2 sepals, 3 mm long and 2 mm wide, ovate, tip attenuate, margin entire, glabrous and Purple 76D inside and out.

*Pistil description*.—One, linear and 17 mm long, Yellow Green 147 tinted Greyed Orange 177B overall, ovary 7 mm long and 1.5 mm wide, style 9.5 mm long, stigma is arrow-shaped, 0.5 mm wide.

*Stamen description*.—2 in number, compound with 3 partially fused sections in each inner petal, 18 mm long, filaments 17 mm long and to 3 mm wide, Red Purple 69D, anthers 2 in six sections, 1 mm long, ovoid, Green Yellow 1D, pollen Yellow 11D.

*Fragrance*.—Slight, sweet.

*Lastingness*.—A raceme blooms for about 4 weeks on the plant.

Fruit and seed: No seed or fruit has been observed to date.

Pest and disease tolerance: The new cultivar is typical to the genus. No known resistances to pests or diseases. No problems have been found in Canby, Oreg.

I claim:

1. A new and distinct form of *Dicentra* plant as hereby illustrated and described.

* * * * *

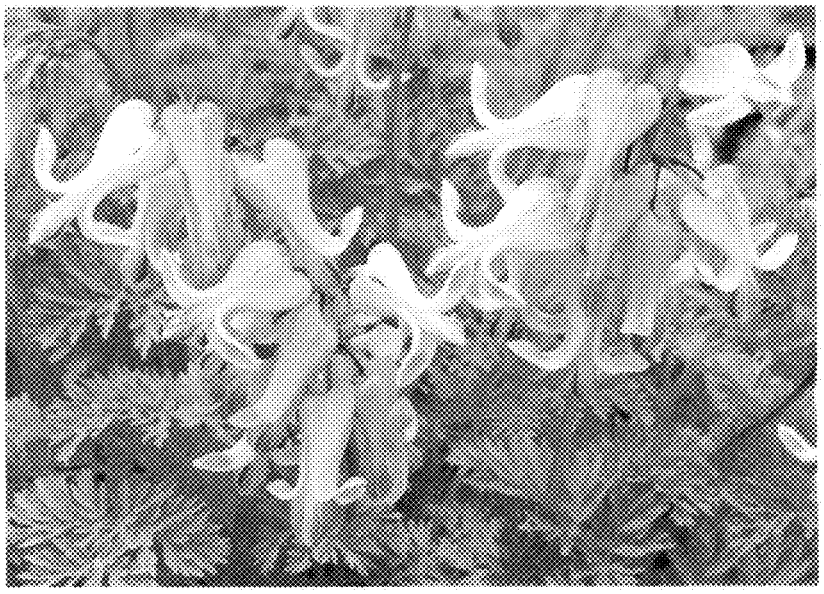

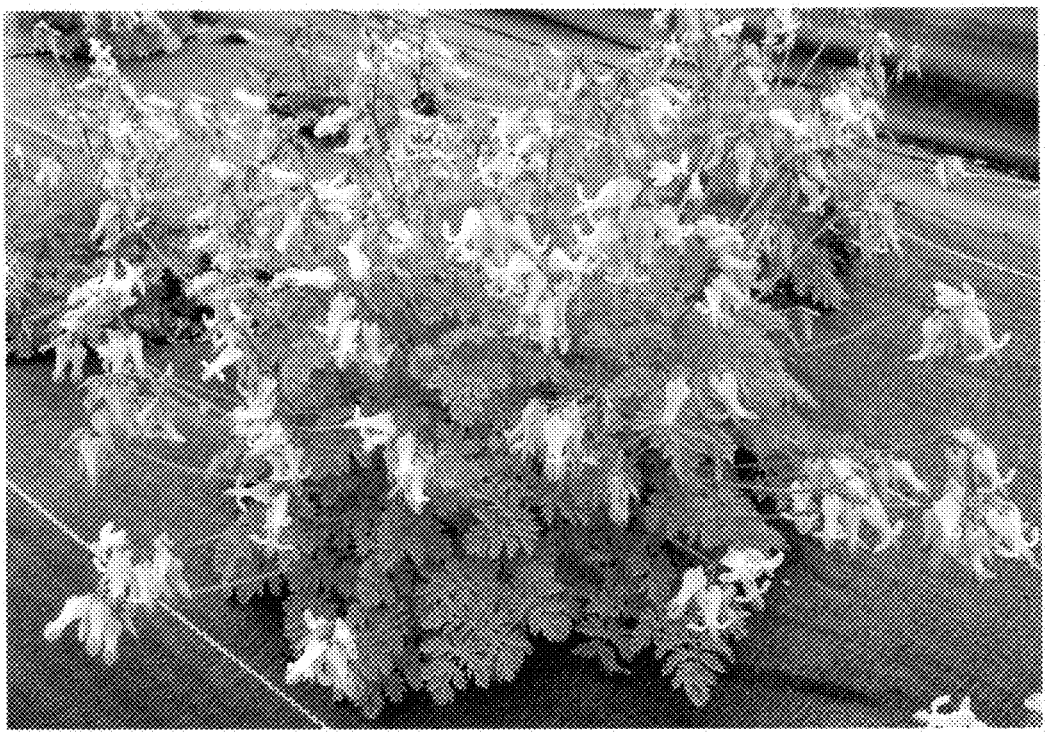
FIG. 1 above, FIG. 2 below